| United States Patent [19] | [11] Patent Number: 4,587,257 |
|---|---|
| DeSantis et al. | [45] Date of Patent: May 6, 1986 |

[54] CONTROL OF OCULAR BLEEDING USING CLONIDINE DERIVATIVES

[75] Inventors: Louis M. DeSantis, Fort Worth; Joseph M. deFaller, Bedford; Billie M. York, Jr., Fort Worth, all of Tex.

[73] Assignee: Alcon Laboratories, Inc., Forth Worth, Tex.

[21] Appl. No.: 682,593

[22] Filed: Dec. 14, 1984

[51] Int. Cl.$^4$ .............................................. A61K 31/415
[52] U.S. Cl. ...................................... 514/392; 514/912
[58] Field of Search ................................ 514/392, 912

[56] References Cited

U.S. PATENT DOCUMENTS

| 3,202,660 | 8/1965 | Zeile et al. | 260/254 |
|---|---|---|---|
| 3,468,887 | 9/1969 | Stähle et al. | 260/253 |
| 3,595,961 | 7/1971 | Stähle et al. | 424/273 |
| 3,666,861 | 5/1972 | Zaimis et al. | 424/273 |
| 4,166,859 | 9/1979 | Stähle et al. | 424/273 R |
| 4,213,995 | 7/1980 | Stähle et al. | 548/315 |
| 4,461,904 | 7/1984 | York | 548/315 |
| 4,515,800 | 5/1985 | Cavero et al. | 514/392 |
| 4,517,199 | 5/1985 | York | 514/392 |

OTHER PUBLICATIONS

J. Med. Chem. 19(8), 1049–54, (1976)–Rouot et al.

*Primary Examiner*—Douglas W. Robinson
*Attorney, Agent, or Firm*—Lowe, Price, LeBlanc, Becker & Shur

[57] ABSTRACT

A method of controlling anterior segment ocular bleeding is described. The method utilizes various clonidine derivatives (e.g., p-aminoclonidine) as the hemostatic agent.

21 Claims, No Drawings

CONTROL OF OCULAR BLEEDING USING CLONIDINE DERIVATIVES

BACKGROUND OF THE INVENTION

1. Field of the Invention

This invention relates to the use of certain clonidine derivatives to control ocular bleeding, such as the bleeding which occurs during opthalmic surgery. More particularly, the present invention relates to the use of hemostatic compositions containing clonidine derivatives (e.g., p-aminoclonidine) to decrease blood flow in the eye and thereby decrease bleeding resulting from ophthalmic surgery or other forms of ocular trauma.

2. Discussion of Related Art

The use of lasers in ophthalmic surgery is a fairly recent development in this field. Ophthalmic surgical procedures using lasers have been found to have numerous advantages over the more conventional techniques previously utilized.

There are many types of lasers currently known and in use, as well as those currently under development. The argon laser has heretofore been the principal type of laser utilized in ophthalmic surgery. The argon laser offers advantages over more conventional ophthalmic surgical instruments, but does suffer from some drawbacks. The use of other types of lasers in ophthalmic surgery has been and will continue to be the subject of scientific investigations directed to overcoming these drawbacks. Two other types of lasers which have been used experimentally are the YAG and Ruby Q-switched lasers.

The YAG and Ruby Q-switched lasers have been found to offer advantages over the argon laser. For example, it has been found that these lasers, unlike the argon laser, do not generate any significant amount of thermal energy in the eye during the surgical procedure. This characteristic is significant, since the thermal energy or heat generated in the eye by the argon laser can lead to tissue damage. However, it has also been discovered that the lack of heat generation by the YAG and Ruby Q-switched lasers results in a greater degree of bleeding during ophthalmic surgery. For example, it has been found that approximately 45% of human glaucoma patients undergoing iridotomies experience iris bleeding when the YAG and Ruby Q-switched lasers are utilized. The occurrence of bleeding from any vessel into the eye constitutes a significant complication during ophthalmic surgical procedures. For example, bleeding from the anterior segment of the eye is a complication which may result in compromised vision following an otherwise successful surgical procedure. Accordingly, a need exists for an ophthalmic hemostatic agent which is capable of decreasing ocular bleeding during surgical procedures utilizing this new generation of lasers.

The above-discussed ophthalmic surgical procedures utilizing laser technology may generally be described as "noninvasive." Ocular bleeding also constitutes a significant complication in the more conventional, invasive surgical procedures. Vasoconstrictors such as phenylepherine have been commonly used in some types of invasive ophthalmic surgery to produce mydriasis prior to the surgical procedure, with any ocular vasoconstriction which may have occurred being an incidental benefit. Unfortunately, mydriasis is to be avoided in patients suffering from glaucoma, and consequently the use of compounds having mydriatic properties is contraindicated in these patients. Accordingly, a need also exists for a hemostatic agent which is suitable for use in invasive ophthalmic surgery and does not cause mydriasis.

Although the foregoing discussion relates to the need for a hemostatic agent in ophthalmic surgical procedures, it is readily apparent that such agents would also be useful in many other ophthalmic conditions involving bleeding.

SUMMARY OF THE INVENTION

A principal object of the present invention is the provision of a method for reducing bleeding during ophthalmic surgical procedures.

A further object of this invention is the provision of topical hemostatic compositions which restrict blood flow through the anterior vasculature of the eye, do not affect the retinal vasculature, are hypotensive, and do not cause mydriasis at clinical concentrations, as well as the provision of a method of preventing ocular bleeding using these compositions.

The foregoing objects as well as other general objects of the present invention are achieved by providing a method of controlling ocular bleeding which comprises topically applying a composition containing a clonidine derivative to the affected eye.

Detailed Description of the Invention

The present invention utilizes certain clonidine derivatives to control hemorrhage of the anterior segment vasculature of the eye during invasive or noninvasive ophthalmic surgery. Clonidine is a known hypotensive compound, and is described, for example, in U.S. Pat. No. 3,202,660; the contents of this patent relating to the structure, preparation and physical properties of this compound are incorporated herein by reference.

It has been previously discovered that certain derivatives of this compound are effective in lowering intraocular pressure when applied topically to the eye. This discovery is described in U.S. Pat. No. 4,461,904, the entire contents of which are incorporated herein by reference. The clonidine derivatives described in this patent are 2-(trisubstituted phenylimino)-imidazoline compounds, which are also known as 2-(trisubstituted anilino)-1,3-diazacyclopentene-(2) compounds. Reference is made to this patent for further details concerning the structure, preparation and physical properties of these clonidine derivatives. Related developments in connection with the above-cited discovery are described in U.S. Pat. Nos. 4,517,199 and 4,515,800 in a commonly assigned application Ser. No. 590,464, filed Mar. 16, 1984. The entire contents of these applications are also incorporated herein by reference.

A preferred group of 2-(trisubstituted phenylimino)-imidazoline compounds having the above-described hemostatic utility are those of formula:

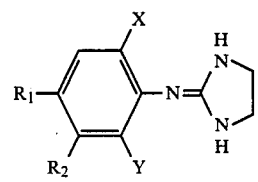

(I)

wherein: $R_1$ and $R_2$ are selected from H, OH, NHR and

with R' being selected from H and $C_1$-$C_4$ alkyl, provided that one of $R_1$ and $R_2$ is hydrogen; and X and Y are selected from Br, Cl, $CH_3$ and $CH_2CH_3$. Specific examples of compounds from this group are set forth in Table 1 below:

TABLE 1

| Compound | $R_1$ | $R_2$ | X | Y |
| --- | --- | --- | --- | --- |
| 1 | $NHCH_3$ | H | $CH_3$ | $CH_3$ |
| 2 | $NHCH_3$ | H | $CH_2CH_3$ | $CH_2CH_3$ |
| 3 | $NHCH_3$ | H | Cl | Cl |
| 4 | $NH_2$ | H | Br | Br |

A group of especially preferred clonidine derivatives of formula (I) are those in which $R_1$ and $R_2$ are selected from H and $NH_2$, provided that one of $R_1$ and $R_2$ is H, and X and Y are selected from Cl, $CH_3$, and $CH_2CH_3$. Specific examples of compounds from this group are set forth in Table 2 below:

TABLE 2

| Compound | $R_1$ | $R_2$ | X | Y |
| --- | --- | --- | --- | --- |
| 5 | H | $NH_2$ | $CH_3$ | $CH_3$ |
| 6 | $NH_2$ | H | $CH_2CH_3$ | $CH_2CH_3$ |
| 7 | H | $NH_2$ | Cl | Cl |
| 8 | $NH_2$ | H | $CH_2CH_3$ | Cl |
| 9 | $NH_2$ | H | $CH_3$ | Cl |
| 10 | $NH_2$ | H | $CH_2CH_3$ | $CH_3$ |
| 11 | $NH_2$ | H | $CH_3$ | $CH_3$ |
| 12 | H | $NH_2$ | $CH_2CH_3$ | $CH_2CH_3$ |
| 13 | $NH_2$ | H | Cl | Cl |

Of these specific examples, p-aminoclonidine (i.e., compound 13) has been found to be particularly well-suited for use in the present invention.

Another preferred group of clonidine derivatives having the above-described hemostatic utility are those of formula:

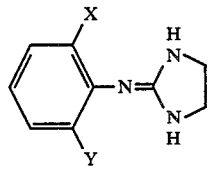
(II)

wherein: X and Y are selected from Br, Cl, $CH_3$ and $CH_2CH_3$, with the provision that at least one of X and Y is alkyl. Compounds of this type are described, for example, in U.S. Pat. No. 3,468,887, and *J. Med. Chem.*, Vol. 19, pages 1049–54 (1976); the contents of these publications relating to the structure, preparation and physical properties of these compounds are incorporated herein by reference. Specific examples of compounds from this group are set forth in Table 3 below:

TABLE 3

| Compound | X | Y |
| --- | --- | --- |
| 14 | $CH_2CH_3$ | $CH_2CH_3$ |
| 15 | $CH_2CH_3$ | $CH_3$ |
| 16 | Cl | $CH_2CH_3$ |

There are no other preferences respecting the clonidine derivatives which may be utilized in this invention, so long as the derivatives selected are capable of restricting blood flow through the anterior vasculature of the eye without affecting the retinal vasculature or causing mydriasis when topically applied to the eye at the clinical concentrations described below.

The above-described compounds may be effectively utilized as hemostatic agents when applied topically to the eye in a concentration of from about 0.05% to 5% by weight. The compounds may be incorporated into various types of ophthalmic formulations according to known techniques. Ophthalmic solutions and suspensions are the preferred dosage forms. Typically such dosage forms are adjusted to isotonicity with sodium chloride. Thickening agents such as carboxymethylcellulose, or carbopol may also be employed to enhance delivery. The pH of such dosage forms is typicaly adjusted to be within the range of 6.0 to 8.0 with HCl or NaOH.

It is contemplated that the compounds will normally be applied preoperatively in order to provide decreased blood flow in the anterior vasculature over a relatively short period (i.e., 3–24 hours) prior to the surgical procedure. However, the compounds may also be applied, for example, in a series of multiple doses following surgery in order to control postsurgical bleeding, or may be applied to control bleeding which is incidental to some other type of ocular procedure or injury. In short, it is contemplated that a number of different uses of the above-described compounds for ocular hemostatis will be developed. Accordingly, the present specification should not be interpreted as limiting the inventive use of these compounds to only surgically-related procedures.

The invention has been described herein with reference to certain preferred embodiments. However, as obvious variations thereon will become apparent to those skilled in the art, the invention is not to be considered as limited thereto.

What is claimed is:

1. A method for the control of ocular bleeding in the eye of a human being which comprises topically applying to an affected eye an ophthalmic formulation containing an hemostatically effective amount of an imidazoline compound of the formula:

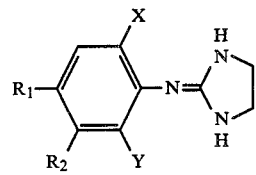
(I)

wherein: $R_1$ and $R_2$ are selected from the group consisting of H, OH, and NHR', wherein R' is selected from the group consisting of H and $C_1$-$C_4$ alkyl, provided that one of $R_1$ and $R_2$ is always hydrogen; and X and Y are selected from the group consisting of Br, Cl, $CH_3$ and $CH_2CH_3$ or a pharmaceutically acceptable free base or acid salt thereof.

2. The method of claim 1 wherein $R_1$ is $NHCH_3$, $R_2$ is H, X is $CH_3$ and Y is $CH_3$.

3. The method of claim 1 wherein $R_1$ is $NHCH_3$, $R_2$ is H, X is $CH_2CH_3$ and Y is $CH_2CH_3$.

4. The method of claim 1 wherein $R_1$ is $NHCH_3$, $R_2$ is H, X is Cl and Y is Cl.

5. The method of claim 1 wherein $R_1$ is $NH_2$, $R_2$ is H, X is Br and Y is Br.

6. The method of claim 1 wherein $R_1$ and $R_2$ are selected from H and $NH_2$, and X and Y are selected from Cl, $CH_3$ and $CH_2CH_3$.

7. The method of claim 6 wherein $R_1$ is H, $R_2$ is $NH_2$, X is $CH_3$ and Y is $CH_3$.

8. The method of claim 6 wherein $R_1$ is $NH_2$, $R_2$ is H, X is $CH_2CH_3$ and Y is $CH_2CH_3$.

9. The method of claim 6 wherein $R_1$ is H, $R_2$ is $NH_2$, X is Cl and Y is Cl.

10. The method of claim 6 wherein $R_1$ is $NH_2$, $R_2$ is H, X is $CH_2CH_3$ and Y is Cl.

11. The method of claim 6 wherein $R_1$ is $NH_2$, $R_2$ is H, X is $CH_3$ and Y is Cl.

12. The method of claim 6 wherein $R_1$ is $NH_2$, $R_2$ is H, X is $CH_2CH_3$ and Y is $CH_3$.

13. The method of claim 6 wherein $R_1$ is $NH_2$, $R_2$ is H, X is $CH_3$ and Y is $CH_3$.

14. The method of claim 6 wherein $R_1$ is H, $R_2$ is $NH_2$, X is $CH_2CH_3$ and Y is $CH_2CH_3$.

15. The method of claim 6 wherein $R_1$ is $NH_2$, $R_2$ is H, X is Cl and Y is Cl.

16. The method of claim 1 wherein the 2-(trisubstituted phenylimino)-imidazoline compound is applied to the eye in a concentration of from about 0.05% to 5% by weight.

17. A method for the control of ocular bleeding in the eye of a human being which comprises topically applying to the affected eye an ophthalmic formulation containing an hemostatically effective amount of a compound of the formula:

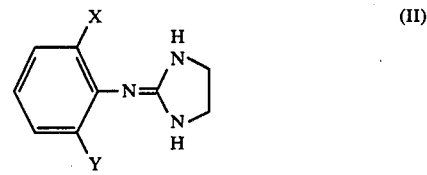

wherein: X and Y are selected from the group consisting of Br, Cl, $CH_3$ and $CH_2CH_3$, with the provision that at least one of X and Y is alkyl, or a pharmaceutically acceptable free base salt thereof.

18. The method of claim 17 wherein both X and Y are $CH_2CH_3$.

19. The method of claim 17 wherein X is $CH_2CH_3$ and Y is $CH_3$.

20. The method of claim 17 wherein X is Cl and Y is $Ch_2CH_3$.

21. The method of claim 17 wherein the compound of formula (II) is applied to the eye in a concentration of from about 0.05% to 5% by weight.

* * * * *